US008202554B2

(12) United States Patent
Kim et al.

(10) Patent No.: US 8,202,554 B2
(45) Date of Patent: Jun. 19, 2012

(54) EXTRACT OF THE FAMILY DIOSCOREACEAE AND COMPOSITION FOR PREVENTING OR TREATING PERIPHERAL NEUROPATHY COMPRISING THE SAME

(76) Inventors: Sun-Yeou Kim, Seoul (KR); Tong-Ho Kang, Seoul (KR); Ji-Ho Park, Seoul (KR)

( * ) Notice: Subject to any disclaimer, the term of this patent is extended or adjusted under 35 U.S.C. 154(b) by 194 days.

(21) Appl. No.: 12/659,051

(22) Filed: Feb. 24, 2010

(65) Prior Publication Data

US 2010/0159043 A1    Jun. 24, 2010

Related U.S. Application Data

(63) Continuation of application No. 12/084,149, filed as application No. PCT/KR2006/004408 on Oct. 27, 2006, now abandoned.

(30) Foreign Application Priority Data

Oct. 28, 2005  (KR) .................. 10-2005-0102450

(51) Int. Cl.
    A61K 36/00     (2006.01)
    A61K 36/8945   (2006.01)
(52) U.S. Cl. ...................... 424/725; 424/773
(58) Field of Classification Search .................. None
    See application file for complete search history.

(56) References Cited

U.S. PATENT DOCUMENTS

| 6,083,941 | A | 7/2000 | Farb | |
|---|---|---|---|---|
| 6,593,301 | B1 * | 7/2003 | Ma et al. .................... | 514/26 |
| 2004/0126447 | A1 * | 7/2004 | Wu .............................. | 424/773 |
| 2005/0019435 | A1 * | 1/2005 | Young ......................... | 424/756 |

FOREIGN PATENT DOCUMENTS

| CN | 1415625 A | 5/2003 |
|---|---|---|
| CN | 1416816 A | 5/2003 |
| CN | 1560061 A | 1/2005 |
| KR | 2000-0008809 | 2/2000 |
| KR | 2003-0020585 | 3/2003 |
| KR | 10-2004-001699 | 1/2004 |
| KR | 10-2005-0111400 | 11/2005 |
| WO | WO 03/082893 A2 | 10/2003 |

OTHER PUBLICATIONS

Coelho et al, A study of 159 Portuguese patients with familial amyloidotic polyneuropathy (FAP) whose parents were both unaffected, Journal of medical genetics, (Apr 1994) vol. 31, No. 4, pp. 293-9.*
Introduction of polyneuropathy from Wikipedia, accessed on Sep. 24, 2010, pp. 1-8.*
Marine et al Gene therapy for the treatment of sensory neuropathy, Expert opinion on biological therapy, (May 2006) vol. 6, No. 5, pp. 499-507.*
Yo-ichi et al, Transthyretin-derived amyloid deposition on the gastric mucosa in domino recipients of familial amyloid polyneuropathy liver, Liver transplantation : official publication of the American Association for the Study of Liver Diseases and the International Liver Transplantation Society, (Feb. 2007) vol. 13, No. 2, pp. 215-218.*
Souayab et al, Asymmetric phenotype associated with rare myelin protein zero mutation, Journal of clinical neuromuscular disease, (Mar. 2010) vol. 11, No. 3, pp. 110-113.*
Vedanarayanan et al, Lethal neonatal autosomal recessive axonal sensorimotor polyneuropathy, Muscle & nerve, (Nov. 1998) vol. 21, No. 11, pp. 1473-1477.*
Jonsen et al, Family members' experience of familial amyloidotic polyneuropathy disease—an infernal struggle and a fact of life, Journal of advanced nursing, (Feb. 2000) vol. 31, No. 2, pp. 347-353.*
Badurska et al, Congenital polyneuropathies, Pediatria Polska, (1980) vol. 55, No. 7, pp. 875-883.*
Coelho et al, A study of 159 Portuguese patients with familial amyloidotic polyneuropathy (FAP) whose parents were both unaffected, Journal of medical genetics, (Apr 1994) vol. 31, No. 4, pp. 293-299.*
Hiroshi et al, Isolation and hypoglycemic activity of Dioscorans A, B, C, D, E, and F; glycans of *Dioscorea japonica* rhizophors, Planta Medica 1986: 168-171.*
Koda-Kimble, M. et al., "Applied Therapeutics: The Clinical Use of Drugs", Applied Therapeutics Inc., 6$^{th}$ ed., 1996, Chapter 48, pp. 48-1-48-62.
Berge, S.M. et al., "Pharmaceutical Salts", Journal of Pharmaceutical Sciences, Jan. 1977, pp. 1-19, vol. 66, No. 1.
Raff, M.C. et al., "Programmed Cell Death and the Control of Cell Survival: Lessons from the Nervous System", Science, Oct. 1993, pp. 695-700, vol. 262.
Ma, C. et al., "Neuroprotective and Antioxidant Activity of Compounds from the Aerial Parts of *Dioscorea* opposite", J. Nat. Prod., 2005, pp. 1259-1261, vol. 68, No. 8.
Van Dam, P.S., "Oxidative stress and diabetic neuropathy: pathophysiological mechanisms and treatment perspectives", Diabetes/Metabolism Research and Reviews, 2002, pp. 176-184, vol. 18.
Hefti, F., "Nerve Growth Factor Promotes Survival of Septal Cholinergic Neurons After Fimbrial Transections", The Journal of Neuroscience, Aug. 1986, pp. 2155-2162, vol. 6, No. 8.
Levi-Montalcini, R. et al., "Destruction of the Sympathetic Ganglia in Mammals By an Antiserum to a Nerve-Growth Protein", Natl. Acad. Sci. USA, 1960, pp. 384-391, vol. 46.
Apfel, S.C. et al., "Efficacy and Safety of Recombinant Human Nerve Growth Factor in Patients with Diabetic Polyneuropathy", J. of Am. Med. Association, 2000, pp. 2215-2221, vol. 284, No. 17.

(Continued)

*Primary Examiner* — Qiuwen Mi
(74) *Attorney, Agent, or Firm* — The Nath Law Group; Joshua B. Goldberg; Mih Suhn Koh (57) ABSTRACT

An extract of the family Dioscoreaceae useful for preventing or treating the peripheral neuropathy; and a pharmaceutical composition or food composition comprising the extract are provided. In addition, a pharmaceutical composition or food composition useful for preventing or treating the peripheral neuropathy comprising a compound isolated from the extract of the family Dioscoreaceae is provided.

7 Claims, 5 Drawing Sheets

OTHER PUBLICATIONS

Kwon et al., "Anti-obesity effect of *Dioscorea nipponica* Makino with lipase-inhibitory activity in rodents", Biosci. Biotechnol. Biochem., 2003, pp. 1451-1456, vol. 67, No. 7.

Li Rui, et al., "HPLC-MS Analysis of Chemical Constituents from *Dioscorea nipponica*," Journal of Instrumental Analysis, Sep. 2004, pp. 33-35, vol. 23.

Nishizawa Machiko et al., Journal of the Neurological Science, vol. 132, No. 2, 1995, pp. 177-181.

Yang Deng-Jye et al., Journal of Argiculture and Food Chemistry, vol. 51, No. 22, Oct. 22, 2003, pp. 6438-6444.

Kim Namho et al., Journal of Ethnopharmacology, vol. 137, No. 1, Sep. 1, 2011, pp. 312-319.

Choi, Sang-Zin et al., Archives of Pharmacal Research, vol. 34, No. 6, Jun. 2011, pp. 865-867.

Kang T. et al., Biol. Pharm. Bull, vol. 34, No. 9, Sep. 2011, pp. 1493-1498.

\* cited by examiner

EXTRACT OF THE FAMILY DIOSCOREACEAE AND COMPOSITION FOR PREVENTING OR TREATING PERIPHERAL NEUROPATHY COMPRISING THE SAME

This is a Continuation Application of U.S. patent application Ser. No. 12/084,149, filed Apr. 25, 2008, which was filed under 35 U.S.C. 371 as a national stage of PCT/KR2006/004408, filed Oct. 27, 2006, an application claiming foreign priority benefits under 35 U.S.C. 119 of Korean Application No. 10-2005-0102450, filed Oct. 28, 2005, the content of each of which is hereby incorporated by reference in its entirety.

TECHNICAL FIELD

The present invention relates to an extract of the family Dioscoreaceae for preventing or treating the peripheral neuropathy; and a pharmaceutical composition or food composition comprising the extract or a compound isolated from the extract.

BACKGROUND ART

Neuropathy is a disease caused by structural or functional abnormalities of the nervous system. The nervous system is divided into the central nervous system which is distributed in the brain and the spinal cord and involved in controlling their functions, and the peripheral nervous system which is distributed in almost all organs excluding the brain and the spinal cord and involved in controlling their functions. The peripheral nervous system is subdivided into the motor nervous system, the sensory nervous system, the autonomic nervous system. A peripheral nerve, where neurites branch out beyond the brain and the spinal cord to the body, arms, and legs, transmits sensation felt at arms and legs to the central nerve (brain and spiral cord), and transmits orders of the central nerve to muscles.

The peripheral nerve can be injured by various causes, which is called collectively as the peripheral neuropathy. The mono-neuropathy refers to a case in which a single peripheral nerve is injured, and the multiple neuropathy refers to a case in which many peripheral nerves are injured to a similar level. The mono-neuropathy usually occurs when a single peripheral nerve is abnormally pressed or traumatically injured during extending to ends of arms and legs. The mono-neuropathy can be treated with operations.

The multiple neuropathy can be induced by various causes, such as metabolic diseases (e.g., diabetes, renal failure, hypothyroidism), drugs (e.g., antitumor agents, antituberculosis drugs) or toxic substance intoxication (e.g., Pb, organic solvents), mal-nutrition (e.g., vitamin deficiency, alcoholism), connective tissue disorders (e.g., rheumatoid arthritis, systemic lupus erythematosus), inflammatory diseases (Guillain-Barre syndrome), or genetically determined neuropathy. In addition, the multiple neuropathy can be caused by cancers.

Until now, the neuropathy has been treated with drugs used as a symptomatic therapy that improves symptoms only and there are almost no fundamental remedies for the neuropathy. Only epalrestat, an aldose reductase inhibitor, was approved by US Food and Drugs Administration (FDA), with respect to diabetic peripheral neuropathy, one of the multiple neuropathies, but epalrestat is not used due to its low therapeutic effects (Foster D W., *Harrison's Principles of Internal Medicine* 13, p 1979, 1999; Stephen L D, *Applied Therapeutics: the clinical use of drugs.* 6, p 48.1-48.62, 1996).

Meanwhile, a protein that affects the growth, differentiation, and survival of neurons in the central nervous system (CNS) and the peripheral nervous system (PNS) is called collectively as a neurotrophic factor (NF), which is one of neuron control factors that regulate the growth, differentiation, and death of neurons. Examples of the NF include a brain-induced neurotrophic factor (BDNF), neurotrophin-3 (NT-3), NT-4, and NT-5. These NFs are synthesized at different areas, and have different differentiation, different expression, and different target regions.

A nerve growth factor (NGF), one of the NFs, inhibits the degeneration and death of neurons so as to prevent a decrease in the number of neurons, to protect neurons from damages, and to retain mature neuron sources (Hefti F., *J. Neurosci.*, 6(8), pp 2155-2162, 1986; and Levi-Montalcini R., et al., *Proc. Natl. Acad. Sci. USA*, 46, pp 384-391, 1960). It is known that when the nervous system normally develops, about 50% of neurons on growth are removed by cell death (Raff M C., et al., *Science*, 262(5134), pp 695-70, 1993), and that NGFs secreted by a target cell determine survival of neurons. In order for neurons to survive, grow, and differentiate in a normal state, a growth factor, such as the NGF, is necessarily required.

Such feasibility of the NGF has led development of a recombinant human nerve growth factor in order to treat a diabetic neuropathy, one of the multiple neuropathies. However, the recombinant human nerve growth factor is still unsatisfactory in safety and efficacy (Apfel S C et al., *Journal of American Medical Association* 284(17), pp 2215-2221, 2000).

DISCLOSURE OF INVENTION

Technical Problem

The present invention provides herbal extracts and compounds isolated therefrom useful for preventing or treating the peripheral neuropathy induced by various causes.

That is, the present invention provides an extract of the family Dioscoreaceae for preventing or treating the peripheral neuropathy.

The present invention also provides a pharmaceutical composition or food composition comprising the extract or a compound isolated from the extract as an active ingredient.

Technical Solution

According to an aspect of the present invention, there is provided an extract of a family Dioscoreaceae for preventing or treating the peripheral neuropathy, the family Dioscoreaceae being at least one selected from the group consisting of *Dioscorea nipponica*, *Dioscorea septembloba*, *Dioscorea quinqueoloba*, *Dioscorea batatas*, *Dioscorea japonica*, *Dioscorea bulbifera*, *Dioscorea tokoro*, and *Dioscorea tenuipes*.

According to another aspect of the present invention, there is provided a pharmaceutical composition for preventing or treating the peripheral neuropathy, which comprises a therapeutically effective amount of the extract; and a pharmaceutically acceptable carrier.

According to still another aspect of the present invention, there is provided a food composition for preventing or treating the peripheral neuropathy, which comprises the extract as an active ingredient.

According to still another aspect of the present invention, there is provided a pharmaceutical composition for preventing or treating the peripheral neuropathy, which comprises a therapeutically effective amount of a compound represented by Formula 1 or salt thereof; and a pharmaceutically acceptable carrier:

[Formula 1]

wherein R is a hydrogen atom, a $C_1$-$C_4$ alkyl group, or a saccharide.

According to still another aspect of the present invention, there is provided a food composition for preventing or treating the peripheral neuropathy, which comprises the compound represented by Formula 1 or salt thereof as an active ingredient.

Advantageous Effects

An extract of the family Dioscoreaceae and/or a compound isolated from the extract induces an endogenous nerve growth factor in an organism so that it can be used in a wide range of applications for preventing or treating peripheral neuropathy.

BEST MODE FOR CARRYING OUT THE INVENTION

In the present specification, the term "peripheral neuropathy" refers to a condition of peripheral nerves (motor nerves, sensory nerves, and autonomic verves) injured by various causes. The peripheral neuropathy may be subdivided into the mono-neuropathy and the poly-neuropathy (also called as multiple neuropathy). The multiple neuropathy includes any neuropathy caused by, metabolic diseases (e.g., diabetes, renal failure, hypothyroidism), drugs (e.g., antitumor agents, antituberculosis drugs) or toxic substance intoxication (e.g., Pb, organic solvents), malnutrition (e.g., vitamin deficiency, alcoholism), connective tissue disorders (e.g., rheumatoid arthritis, systemic lupus erythematosus), inflammatory diseases (Guillain-Barre syndrome), or genetically determined neuropathy. In addition, the multiple neuropathy may include a neuropathy caused by genetic factors and cancers.

An extract of the family Dioscoreaceae according to an embodiment of the present invention or a compound isolated from the extract derives neurite outgrowth and increases the amount of an endogenous nerve growth factor secreted, so that nerves of the peripheral nervous system can be effectively differentiated, protected, and reinnervated. In particular, the extract and/or the compound allow oral administration, which improve patients medication compliance.

The present invention provides an extract of the family Dioscoreaceae for preventing or treating the peripheral neuropathy.

The family Dioscoreaceae is at least one selected from *Dioscorea nipponica*, *Dioscorea septembloba*, *Dioscorea quinqueoloba*, *Dioscorea batatas*, *Dioscorea japonica*, *Dioscorea bulbifera*, *Dioscorea tokoro*, and *Dioscorea tenuipes*. Preferably, the family Dioscoreaceae is *Dioscorea nipponica*, *Dioscorea quinqueoloba*, and/or *Dioscorea tokoro*. More preferably, the family Dioscoreaceae is *Dioscorea nipponica*.

The extract according to the present invention can be obtained through an extraction process which includes extracting a whole part, root, or aerial part (for example, leave or stem) of the family Dioscoreaceae with an extraction solvent (first extraction solvent) selected from the group consisting of water, $C_1$-$C_4$ alcohol, and a mixture of water and a $C_1$-$C_4$ alcohol. For example, the extract of the family Dioscoreaceae can be obtained by extracting the root of the family Dioscoreaceae with the first extraction solvent. The first extraction solvent may be a mixture solvent of water and methanol or a mixture solvent of water and ethanol.

In the extraction process, the whole part, root, or aerial part, preferably, the root of the family Dioscoreaceae is cut into small sections, and then extracted with the first extraction solvent. At this time, the amount of the first extraction solvent may be 1 to 20 times, preferably about 3 to 10 times, greater than that of the family Dioscoreaceae. The first extract solvent may be a mixture solvent of water and methanol (for example, about 85% methanol solution) or a mixture solvent of water and ethanol (for example, about 85% ethanol solution). The extraction is not affected by temperature, and can be performed at various temperature ranges, such as a temperature of 15° C. to 100° C. The extraction can be performed by cold extraction, hot extraction, superfluid extraction, centrifugal extraction, ultrasonic extraction, or reflux cooling extraction. The extraction time may vary according to the extraction method. For example, the extraction can be performed once or multiple times for about 1 hour to 10 days. Preferably, the extraction can be performed twice or three times at room temperature for about 2 days using the first extraction. The extract obtained by extraction with the first extraction solvent can be a liquid form in which impurities in the extract are removed using a conventional method, e.g., filtration, or a powder form obtained by concentrating under reduced pressure or drying the liquid extract using a conventional method.

In addition, when needed, the extraction process may further include obtaining a fraction having higher contents of active ingredients. That is, the extraction process further includes: dispersing the extract obtained by the extraction with the first extraction solvent in water; and extracting the resultant solution with water saturated $C_1$-$C_4$ alcohol (second extraction solvent), thereby increasing the contents of active ingredients in the obtained extract.

When the extract obtained by extracting with the first extraction solvent is dispersed in water, a liquid form per se obtained by the extraction with the first extraction solvent may be dispersed in water, or a powder form obtained by concentrating the liquid extract under reduced pressure and/or drying the liquid extract using a conventional method may be dispersed in water.

The water saturated $C_1$-$C_4$ alcohol (second extraction solvent) may be water saturated butanol.

The present invention includes, within its scope, a composition comprising a compound isolated from the extract, i.e., a steroidal saponin or steroidal sapogenin. That is, the present invention includes a pharmaceutical composition for preventing or treating the peripheral neuropathy, which comprises a therapeutically effective amount of a compound represented by Formula 1 or salt thereof; and a pharmaceutically acceptable carrier:

[Formula 1]

wherein R is a hydrogen atom, a $C_1$-$C_4$ alkyl group, or a saccharide.

In the compound of Formula 1, R may be hydrogen or methyl, preferably hydrogen. That is, the compound of Formula 1 can be 3-β,25R-spirost-5-en-3-ol.

The saccharide can be monosaccharide, disaccharide, or polysaccharide, such as glucose, fructose, mannose, galactose, ribose, cellulose, glycogen, sucrose, maltose, and lactose.

The salt of the compound of Formula 1 can be a conventional inorganic acid and/or organic acid addition salt prepared from steroidal saponin or sapogenin compounds. Examples of the salt of the compound of Formula 1 include salts disclosed in International Laid-open Patent Publication No. WO2003/082893. These salts can be prepared in situ during final separating and purifying processes of a compound. In particular, an acid addition salt can be prepared by reacting a refined compound in a free base form with a suitable organic or inorganic acid and then separating the produced salt (see S. M. Berge, et al., Pharmaceutical Salts, J. Pharm. Sci., 66: p. 1-19(1977)). International Laid-open Patent Publication No. WO2003/082893 and the journal of. M. Berge, et al. are used as a reference in the present invention. A base addition salt can be prepared by reacting a refined compound in an acid form with a suitable organic or inorganic base and separating the produced salt. The base addition salt can be a pharmaceutically acceptable metal or amine salt. The acid addition salt can be a salt prepared from an acid selected from hydrochloric acid, sulfuric acid, phosphoric acid, and nitric acid. The base addition salt can be a salt prepared from a base selected from sodium hydroxide, potassium hydroxide, and ammonium hydroxide.

The compound of Formula 1 can be isolated from the extract according to an embodiment of the present invention, synthesized using a known method (see Herbert O. House, Modern Synthetic Reactions, The Benjamin Cummings Publishing Company, 1972), or commercially obtained (Sigma Co., USA.).

The method for isolating the compound of Formula 1 from the extract may include an acid hydrolysis process and an recrystallization process using the extract obtained according to an embodiment of the present invention (for example, an extract obtained using the first extraction solvent and the second extraction solvent.) For example, the method for isolating the compound of Formula 1 from the extract may include: hydrolyzing with an acid, such as 2.5N hydrochloric acid, at a temperature of 50 to 150° C., preferably at about 94° C., for 30 minutes to 3 days, preferably for about 4 hours; solvent extracting the obtained hydrolysate (that is, aglycone sapogenin) with an organic solvent, such as chloroform, acetone, benzene, or xylene, for 1 to 60 minutes, preferably for about 15 minutes, and then separating the organic layer; when needed, concentrating the separated organic layer at a temperature of 10 to 100° C., preferably 30 to 35° C.; recrystallizing the organic layer or the concentrated solution of the organic layer with $C_1$-$C_4$ alcohol or $C_1$-$C_4$ alcoholic solution (for example, 95% ethanol solution); and, washing the obtained precipitate with water when needed, and recrystallizing with acetone.

The present invention provides a pharmaceutical composition for preventing or treating the peripheral neuropathy, which comprises a therapeutically effective amount of an extract of the family Dioscoreaceae or a compound of Formula 1 or salt thereof; or a pharmaceutically acceptable carrier.

The pharmaceutical composition according to the present invention includes a pharmaceutically acceptable carrier, and can be formulated into oral dosage form, external dosage form, suppository, and sterile injection solution, such as powders, granules, tablets, capsules, suspensions, emulsions, syrups, or aerosols. The pharmaceutically acceptable carrier can be lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, or mineral oil. The pharmaceutical composition may further include a diluent or an excipient, such as filler, expander, binder, humectant, disintegrant, or surfactant. A solid oral formulation can be a tablet, a pill, a powder, a granule, or a capsule. Such solid formulations may include at least one excipient selected from, for example, starch, calcium carbonate, sucrose, lactose, and gelatin. In addition, such solid formulations may further include a lubricant, such as magnesium stearate or talc. A liquid oral formulation can be a suspension, a solution, an emulsion, or syrup. In addition, the liquid oral formulation may include a diluent, such as water, liquid paraffine; humectant; sweetening agent; odorant; or preservative. A parenteral formulation can be a sterile aqueous solution, a non-aqueous solution, a suspension, an emulsion, a lyophilized formulation, or a suppository. Non-aqueous solvents or suspending agents can be propylene glycol, polyethylene glycol, natural oil, such as olive oil, or injectable esters, such as ethylolate. Vehicles for suppository can be witepsol, macrogol, Tween 61, cacao butter, Laurin, or glycerogelatine.

In the pharmaceutical composition according to the present invention, a dose of the extract of the family Dioscoreaceae or the compound of Formula 1 may vary depending on patient's state or body weight, seriousness of disease, dosage forms, administration routes, and the period of administration, and can be appropriately determined by a person having ordinary skill in the art. For example, the extract of the family Dioscoreaceae or the compound of Formula 1 can be administered in an amount of 0.0001 to 1000 mg/kg, preferably 0.001 to 1000 mg/kg, per day. The administration can be completed once or through several times per day. In the pharmaceutical composition according to the present invention, the amount of the extract of the family Dioscoreaceae or the compound of Formula 1 may be in the range of 0.001 to 50% by weight based on 100% by weight of the pharmaceutical composition.

The pharmaceutical composition can be administered to mammals, such as rats, mouse, livestock, or human beings, through various routs, e.g., orally, rectally, intravenously, intramuscularly, subcutaneously, through intrauterine dura mater injection, or through intracerebroventricular injection.

The present invention includes, within its scope, a food composition for preventing or treating the peripheral neuropathy, which comprises an extract of the family Dioscoreaceae or the compound of Formula 1 as an active ingredient.

The food composition according to the present invention can be used as a health functional food. According to Article 6727 of Korean Health Functional Food law, the "health functional food" refers to a food which is produced and processed using a source or component that carries out good functions on the human body. The "function" refers to an intake purporting to attain good health effects, that is, a nutrient control with respect to the structure and function of the human body or a physiological operation.

The food composition according to the present invention can include a conventional food additive. The conformity of the "food additive" is determined, as long as there are no other regulations, in consideration with the standard and criteria of the corresponding item according to the general rule of the food additives codex and general tests approved by Korea Food & Drug Administration.

The items listed on the "food additives codex" include a chemically synthesized substance, such as ketone, glycine, potassium citrate, nicotinic acid, or cinnamic acid; natural additives, such as persimmon color, an extract of licorice, crystalline cellulose, caoliang color, or guar gum; or mixed formulation, such as L-sodium glutamate formulation, alkali additives for noodles, preservatives, or tar color formulation.

The food composition according to the present invention may include the extract of the family Dioscoreaceae or the compound of Formula 1 in an amount of 0.01 to 95% by weight, preferably 1 to 80% by weight, based on 100% by weight of the food composition, in order to prevent and/or treat the peripheral neuropathy. In addition, in order to prevent and/or treat the peripheral neuropathy, the food composition can be produced and processed into tablets, capsules, powder, granule, liquid phase, or pills.

For example, in order to produce a health functional food in a tablet form, a mixture of the extract of the family Dioscoreaceae or the compound of Formula 1, an excipient, a binder, a disintegrant, and other additives can be granulated using a conventional method, and then compression molding process is preformed with a lubricant. Alternatively, the mixture can be directly subjected to the compression molding process. In addition, when needed, the health formulated food in a tablet form may include sweetening agents, and when needed, the health formulated food in a tablet form can be coated with coating materials.

Among health functional foods in a capsule form, a hard capsule formulation can be produced by filling a conventional hard capsule with a mixture of the extract of family Dioscoreaceae or the compound of Formula 1 and an additive, such as an excipient, or granules of the mixture, or coated granules of the mixture; and a soft capsule formulation can be produced by filling a capsule support of gelatin with a mixture of the extract of family Dioscoreaceae or the compound of Formula 1 and an additive, such as an excipient. When needed, the soft capsule formulation can include plasticizer, such as glycerin or sorbitol, a coloring agent, and a preservative.

A health functional food in a pill form can be produced by molding a mixture of the extract of family Dioscoreaceae or the compound of Formula 1, an excipient, a binder, and a disintegrant using a suitable method. When needed, the health functional food in a pill form can be coated with white sugar or other coating materials, or can be covered with starch, talc, or other materials.

A health functional food in a granule form can be produced by granulating a mixture of the extract of family Dioscoreaceae or the compound of Formula 1, an excipient, a binder, and a disintegrant using a suitable method. When needed, the health functional food in a granule form can include a flavoring agent and a sweetening agent.

The excipient, the binder, the disintegrant, the lubricant, the sweetening agent, and the flavoring agent used in the present invention can be defined as corresponding materials having the same or similar functions disclosed in references known in the art (The Korean pharmacopoeia review, Moonsungsa Publication Co., Korea Pharmaceutical University Association, Fifth edition, p 33-48, 1989).

Mode For The Invention

The present invention will be described in further detail with reference to the following examples. These examples are for illustrative purposes only and are not intended to limit the scope of the present invention.

EXAMPLE 1

Preparation of Extract

*Dioscorea Nipponica* was dried and the root thereof was cut into small sections. The 500 g of the sample was added to 10 l of 85% methanol solution and then extracted three times (each for 2 hours) at room temperature. Such an extraction process was repeated twice. The resultant supernatants were collected and concentrated under reduced pressure, thereby obtaining 74 g of a crude extract.

The 74 g of the crude extract was suspended in 1 l of distilled water, 1 l of water-saturated butanol was added thereto, and then, the generated organic layer was separated, which was repeated five times. The obtained organic layers were collected altogether and dried under reduced pressure. As a result, 17 g of the extract of *Dioscorea Nipponica* was obtained.

EXAMPLE 2

Preparation of Extract

*Dioscorea quinqueoloba* was dried and the root thereof was cut into small sections. The 500 g of the sample was added to 5 l of 85% ethanol solution and then extracted three times (each for 2 hours) at room temperature. Such an extraction process was repeated twice. The resultant supernatants were collected and concentrated under reduced pressure, thereby obtaining 90 g of a crude extract.

The 90 g of the crude extract was suspended in 1 l of distilled water, 1 l of water-saturated butanol was added thereto, and then, the generated organic layer was separated, which was repeated five times. The obtained organic layers were collected altogether and dried under reduced pressure. As a result, 26 g of the extract of *Dioscorea quinqueoloba* was obtained.

EXAMPLE 3

Preparation of Extract

*Dioscorea tokoro* was dried and the root thereof was cut into small sections. The 300 g of the sample was added to 3 l of 85% ethanol solution and then extracted three times (each for 2 hours) at room temperature. Such an extraction process was repeated twice. The resultant supernatants were collected and concentrated under reduced pressure, thereby obtaining 35 g of a crude extract.

The 35 g of the crude extract was suspended in 0.5 l of distilled water, 0.5 l of water-saturated butanol was added thereto, and then, the generated organic layer was separated, which was repeated five times. The obtained organic layers were collected altogether and dried under reduced pressure. As a result, 11 g of the extract of *Dioscorea tokoro* was obtained.

EXAMPLE 4

Separation of Active Compound 1 g of the extract of *Dioscorea nipponica* obtained in Example 1 was hydrolyzed at 94° C. for four hours by adding 10 ml of 2.5N HCl 10 ml thereto. Then, the resultant hydrolysate was extracted with 10 ml of chloroform for 15 minutes. The chloroform layer was separated, filtered, and then concentrated under reduced pressure at a temperature of 30-35° C. The obtained residue was recrystallized at 4° C. using 5 ml of 95% ethanol solution. The recrystallized precipitate was filtered, washed with water, recrystallized at 4° C. using 3 ml of acetone, and then filtered to obtain about 100 mg of the precipitate. The precipitate was identified as 3beta, 25R-spirost-5-en-3-ol represented by Formula 2.

[Formula 2]

(1) Formula: $C_{27}H_{42}O_3$
(2) Molecular Weight: 414.62
(3) Melting Point: 204-207° C.
(4) $[\alpha]^{25}_D$-129
(5) NMR Data: refer to Table 1

TABLE 1

| $^{13}$C | Chemical shift $(\delta)^a$ | $^1$H | Chemical shift $(\delta)^a$ |
|---|---|---|---|
| C-1 | 37.6-37.7 | H-1 | 1.60-1.70; 0.87-0.91 (m, o) |
| C-2 | 30.3-30.4 | H-2 | 2.00-2.03; 1.75-1.79(m, o) |
| C-3 | 78.1-78.7 | H-3 | 3.81-3.90(m, J = 4.7-5.6 Hz) |
| C-4 | 38.9-39.5 | H-4 | 2.57-2.29(m, J = 13-14 Hz; J = 5.0; 12.0 Hz) |
| C-5 | 140.9-141.1 | | |
| C-6 | 121.9-122.0 | H-6 | 5.23-5.26(d, J = 4.6-5.4 Hz) |
| C-7 | 32.4-32.5 | H-7 | 1.77-1.82; 1.41-1.46(m, o) |
| C-8 | 31.8-31.9 | H-8 | 1.44-1.48(m, o) |
| C-9 | 50.4-50.5 | H-9 | 0.80-0.83(m) |
| C-10 | 37.2-37.3 | | |
| C-11 | ~21.3 | H-11 | 1.35-1.38(m, o) |
| C-12 | 40.0-40.1 | H-12 | 1.60-1.62(m, o) |
| C-13 | 40.6-40.7 | | |
| C-14 | 56.8-56.8 | H-14 | 1.01(m, o) |
| C-15 | 32.4-32.5 | H-15 | 1.95-1.98(m, J = 5.9-6.1 Hz); 1.31-1.35(m, o) |
| C-16 | 81.3-81.3 | H-16 | 4.45-4.48(m, J = 7.0-7.4 Hz) |
| C-17 | 63.0-63.1 | H-17 | 1.72-1.75(m, o) |
| C-18 | 16.5-16.6 | H-18 | 0.73-0.76(s) |
| C-19 | 19.6-19.6 | H-19 | 0.80-1.00(s) |
| C-20 | 42.1-42.2 | H-20 | 1.88(m) |
| C-21 | 15.2-15.2 | H-21 | 1.05-1.07(d, J = 6.8-7.2 Hz) |
| C-22 | 109.4-109.5 | | |
| C-23 | 32.0-32.0 | H-23 | 1.57-1.63(m, o) |
| C-24 | 29.4-29.5 | H-24 | 1.48-1.52(m, o) |
| C-25 | 30.8-30.8 | H-25 | 1.50(m, o) |
| C-26 | 67.0-67.1 | H-26 | 3.50-3.40(m, J = 10.5; 3.0; 10.5 Hz) |
| C-27 | 17.5-17.5 | H-27 | 0.60-0.63(d, J = 4.7-5.8 Hz) |

EXPERIMENTAL EXAMPLE 1

Measurement of Neurite Outgrowth

In an incubator with conditions including 5% $CO_2$ and a temperature of 37° C., PC 12 cell (pheochromocytoma, ATCC Number: CRL-1721) was cultured in a RPMI 1640 medium supplemented with horse serum (10%, v/v), fetal bovine serum (5%, v/v), and 1% penicillin-streptomycin In order to find the effect of the compound of Formula 2 on the neurite outgrowth, the mediums supplemented with 2% horse serum, 1% fetal bovine serum, and 1% penicillin-streptomycin were added to each 6-well plate coated with poly-d-lysine and then the PC12 cells were inoculated in 5×10⁴ cells each well. After 24 hours, these wells were treated with 10 □/ml of ethanol, 10 □/□ of the compound of Formula 2, and 50 ng/□ of a nerve growth factor (R&D system, USA), respectively. Then, after 48 hours, the length of the neurite was measured using an inverted image contrast microscope (CK-2, Olympus, USA) (See FIG. 1 and FIG. 2)

Figure 1:
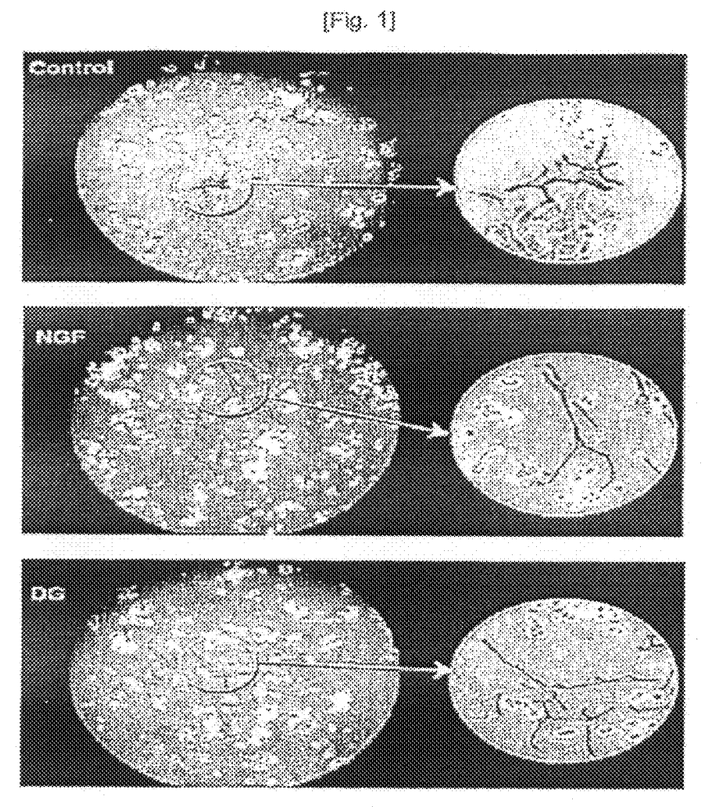
FIG. 1 and FIG. 2 shows the effect of the compound isolated from an extract according to an embodiment of the present invention on neurite outgrowth.
Figure 2:
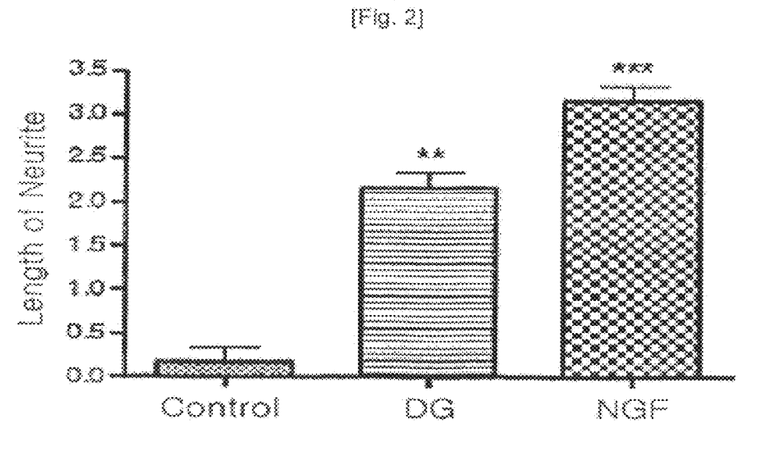

Referring to FIGS. 1 and 2, the neurite outgrowth was not observed in the ethanol-injected group (control), but the neurite outgrowth was induced both in the compound of Formula 2-treated group (DG) and in the nerve growth factor-treated group (NGF). Accordingly, it was found that the compound of Formula 2 induced differentiation of the PC 12 cell by inducing the neurite outgrowth.

EXPERIMENTAL EXAMPLE 2

Measurement of Level of Nerve Growth Factor in Mouse Serum

The compound of Formula 2 was dissolved in 0.2 ml of a solution of dimethyl-sulfoxide:ethanol (3:1), and then orally administered once to 7-week old male ICR mice (n=7) in an amount of 10 mg/kg. After 24 hours, the amount of an endogenous nerve growth factor was measured by ELISA. As a control group, an ICR mouse was orally administered once with 0.2 ml of the dimethylsulfoxide:ethanol (3:1). Then, the amount of a nerve growth factor in the control group was measured in the same manner as described above.

Figure 3:
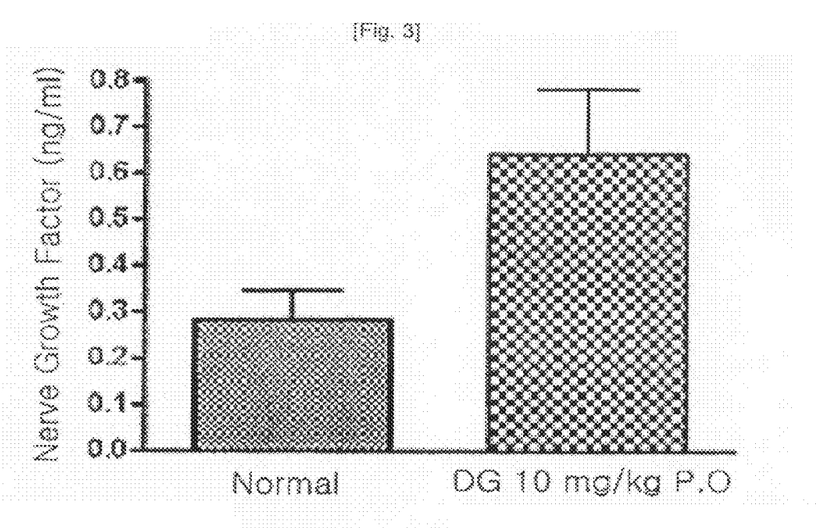
FIG. 3 is a graph illustrating a change in the level of a nerve growth factor (NGF) in normal mouse serum resulting from administration of a compound isolated from an extract according to an embodiment of the present invention.

Referring to FIG. 3, the compound of Formula 2-administered group (DG 10 mg/kg P.O) showed a nerve growth factor in the serum about 2.5 times greater than the control group. Such results show that the compound of Formula 2 can treat the neuropathy by suppressing the degeneration and death of neurons in a mouse and thus preventing a decrease in the number of neurons.

EXPERIMENTAL EXAMPLE 3

Measurement of Level of Nerve Growth Factor in Serum of Diabetes-Induced Mouse An alloxan-induced diabetic mouse was prepared as an animal model having diabetic neuropathy, one of the multiple neuropathies.

7-week old male ICR mice underwent alimentary abstinence for 18 hours, and then alloxan dissolved in a physiological saline was once injected to them by intraperitoneal injection in an amount of 160 mg/kg to induce diabetes. Mice that maintained their fasting blood sugar to 200 mg/dl or more for one week, that is, diabetes-induced mice were selected and then divided into a control group (n=10), an extract-administered group (n=10), and a compound-administered group (n=10). The control group was administered with 0.2 ml of a solution of dimethylsulfoxide:ethanol (3:1), the extract-administered group was administered with the extract obtained according to Example 1 dissolved in a solution of dimethylsulfoxide:ethanol (3:1) in an amount of 100 mg/kg, and the compound-administered group was administered with the compound of Formula 2 dissolved in a solution of dimethylsulfoxide:ethanol (3:1) in an amount of 10 mg/kg. The all groups were orally administered three times per one week, and the entire administration period was one month. The amount of an endogenous nerve growth factor in the serum was measured by ELISA.

Figure 4:
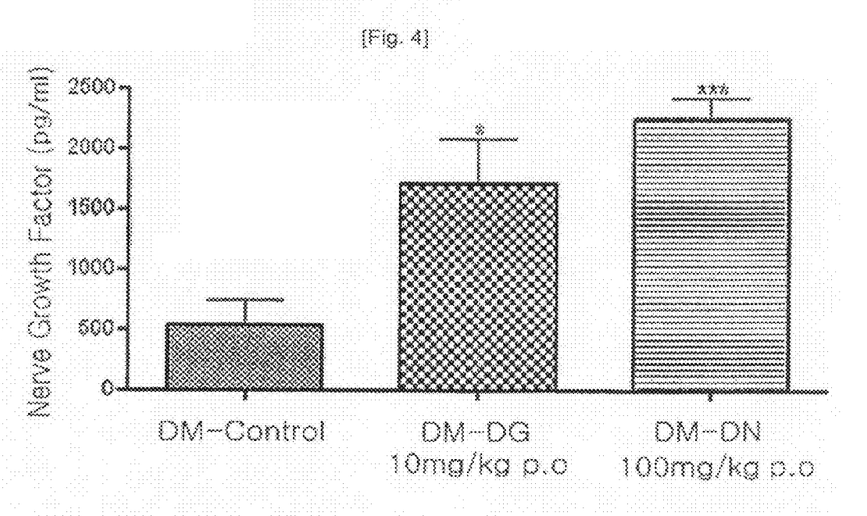
FIG. 4 is a graph illustrating a change in the level of a NGF in the serum of a diabetes-induced mouse resulting from administration of an extract according to an embodiment of the present invention and a compound isolated from the extract.

Referring to FIG. 4, the amounts of the endogenous nerve growth factor in the serum of both the extract-administered group (DN 100 mg/kg p.o) and the compound-administered group (DG 10 mg/kg p.o) were three and four times higher than the control group to which only a vehicle was injected, respectively. Such results show that the extract and compound according to the present invention can treat the diabetic neuropathy by suppressing the degeneration and death of neurons in nerve-injured diseases caused by diabetes and thus preventing a decrease in the number of neurons.

EXPERIMENTAL EXAMPLE 4

Measurement of Transmission Speed of Motor Nerve and Sensory Nerve of Sciatic Nerve in Diabetes-Induced Mouse The therapeutic effect of the compound according to the present invention on the diabetic neuropathy, one of the multiple neuropathies, was identified by measuring the effect of the compound according to the present invention on the transmission speed of the motor nerve and sensory nerve in the sciatic nerve.

7-week old male ICR mice underwent alimentary abstinence for 18 hours, and then alloxan dissolved in a physiological saline was once injected to them by intraperitoneal injection in an amount of 160 mg/kg to induce diabetes. Mice that maintained their fasting blood sugar to 200 mg/dl or more for one week, that is, diabetes-induced mice were selected and then divided into a control group (n=7), and a compound-administered group (n=7). The control group was administered with 0.2 ml of a solution of dimethylsulfoxide:ethanol (3:1), and the compound-administered group was administered with the compound of Formula 2 dissolved in a solution of dimethylsulfoxide:ethanol (3:1) in an amount of 10 mg/kg. 7-week old male ICR mice in which diabetes was not induced were grouped as a normal group (n=7), and the normal group was administered with 0.2 ml of a solution of dimethylsulfoxide:ethanol (3:1). The all groups were orally administered three times per one week, and the entire administration period was 2 months. Administration-completed mice were sacrificed by cervical dislocation, and then the skin and muscle in the femoral region were quickly removed. Then, left and right sciatic nerves were respectively separated in a length of 20 mm or more and stored in a physiological saline while air flows through the physiological saline. The separated sciatic nerves were placed on a 20 mm round measurement plate. Then, a sensor and a stimulating probe were connected to respective neuroterminals and the electrical conductivity was measured using a digital storage oscilloscope to assess the nerve transmission speed (see FIGS. 5 and 6.)

In general, the myelin is a phospholipid membrane surrounding axons with several layers, and also called as myelin sheath. Like the plastic coating of an electric wire, the myelin, through a white lipid material, prevents the electrical signals transmitted by neurons from leaking or dispersing. The myelin is regularly spaced between nodes of ranvier (a portion that forms nodes of myelin) at which the myelin is not formed, and surrounds axons. The electrical signal is transmitted along the space, impulses are quickly transmitted along neurons, and the myelin increases the electrical impulse speed. Accordingly, when the myelin is destructed by nerve injury due to the neuropathy induced by diabetes, axons stops their function and the nerve transmission speed decreases.

Figure 5:
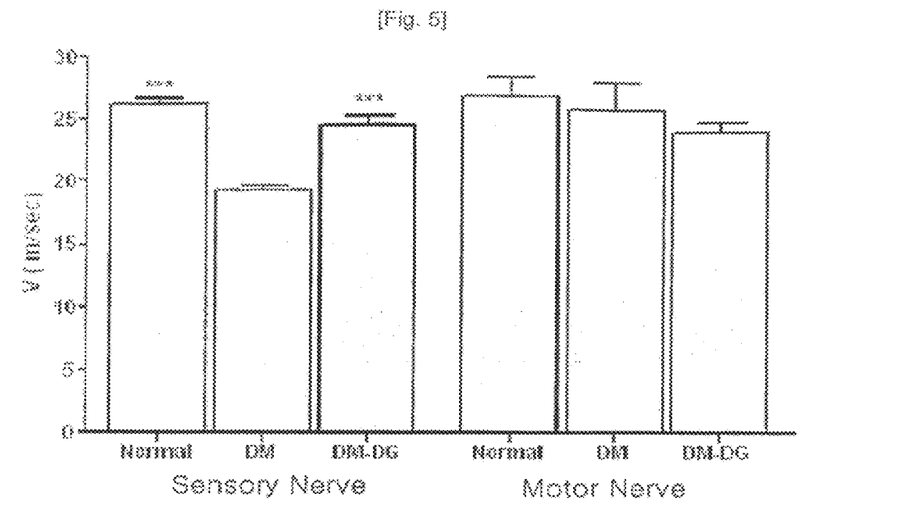
FIG. 5 and FIG. 6 illustrates the effect of a compound isolated from an extract according to an embodiment of the present invention on the transmission speed of the motor nerve and sensory nerve in a sciatic nerve of diabetes-induced mice (FIG. 5: DG treatment for one-month, FIG. 6: DG treatment for two-month)
Figure 6:
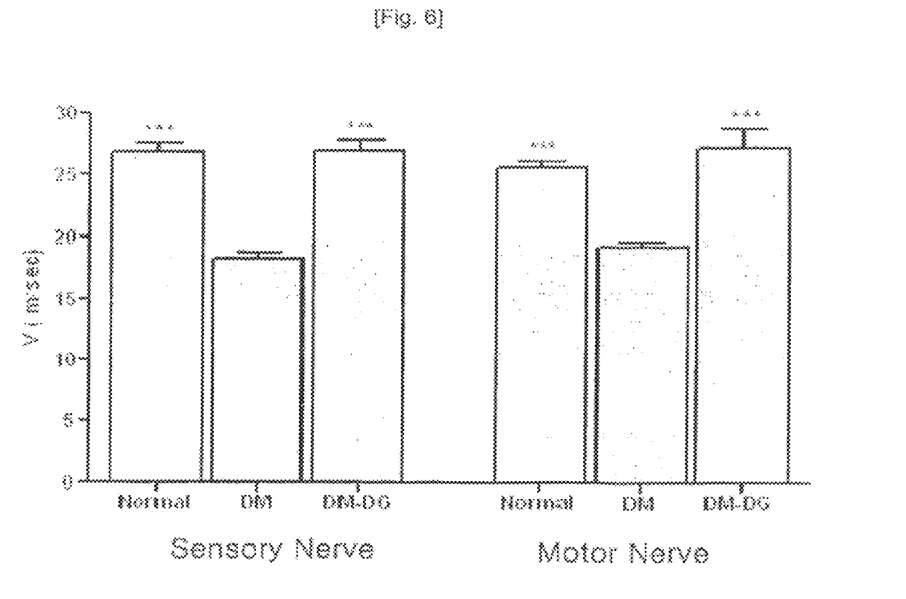

During one month of a diabetes-induced period, the compound-administered group (DM-DG) showed a transmission speed of the sensory nerve 25% higher than the diabetes-induced control group (DM) to which only the vehicle was administered (see FIG. 5). During two months of a diabetes-induced period, the compound-administered group (DM-DG) showed a transmission speed of the sensory nerve 45% higher than the control group, and showed a transmission speed of the motor nerve 40% higher than the control group (see FIG. 6). Accordingly, it was found that the compound according to the present invention has a therapeutic effect on nerve injury due to the diabetic neuropathy by increasing the transmission speed of the sensory nerve and motor nerve of a diabetes-induced mouse.

EXPERIMENTAL EXAMPLE 5

Measurement of Level of Nerve Growth Factor in Sciatic Nerve in Diabetes-Induced Mouse 7-week old male ICR mice underwent alimentary abstinence for 18 hours, and then alloxan dissolved in a physiological saline was once injected to them by intraperitoneal injection in an amount of 160 mg/kg to induce diabetes. Mice that maintained their fasting blood sugar to 200 mg/dl or more for one week, that is, diabetes-induced mice were selected and then divided into a control group (n=5), and a compound-administered group (n=5). The control group was administered with 0.2 ml of a solution of dimethylsulfoxide:ethanol (3:1), and the compound-administered group was administered with the compound of Formula 2 dissolved in a solution of dimethylsulfoxide:ethanol (3:1) in an amount of 10 mg/kg. The all groups were orally administered three times per one week, and the entire administration period was one month. The amount of an endogenous nerve growth factor in the sciatic nerve was measured by ELISA (see FIG. 7)

Figure 7:
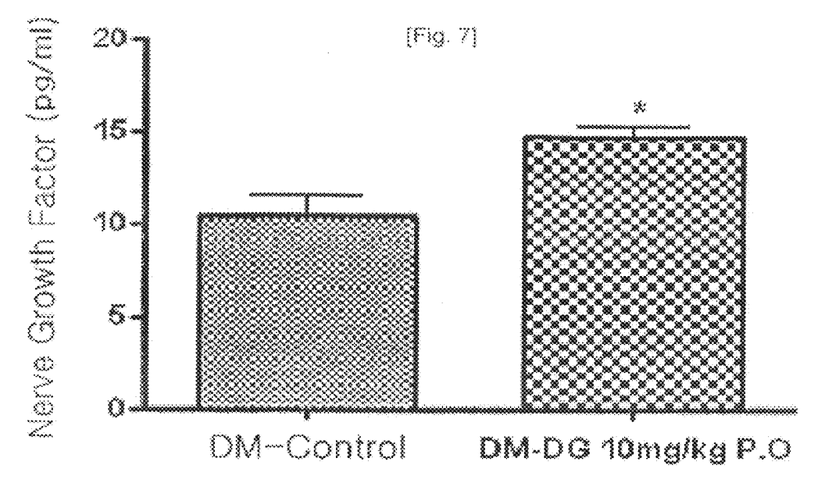
FIG. 7 is a graph illustrating a change in the level of a NGF in the sciatic nerve of a diabetes-induced mouse resulting from administration of a compound isolated from an extract according to an embodiment of the present invention.

Referring to FIG. 7, it was found that the nerve growth factor in the sciatic nerve of the compound-administered group (DM-DG 10 mg/kg P.O) was about 30% higher than that of the control group to which only the vehicle was injected. Accordingly, it is considered that the results shown in FIGS. 5 and 6 result from the nerve protecting function of the nerve growth factor.

EXPERIMENTAL EXAMPLE 6

Measurement of Change in Amount of Sorbitol in Sciatic Nerve of Diabetes-Induced Mouse The therapeutic effect of the compound according to the present invention on the neuropathy was identified by measuring a change in the amount of sorbitol in the sciatic nerve.

7-week old male ICR mice underwent alimentary abstinence for 18 hours, and then alloxan dissolved in a physiological saline was once injected to them by intraperitoneal injection in an amount of 160 mg/kg to induce diabetes. Mice that maintained their fasting blood sugar to 200 mg/dl or more for one week, that is, diabetes-induced mice were selected and then divided into a control group (n=3), and a compound-administered group (n=3). The control group was administered with 0.2 ml of a solution of dimethylsulfoxide:ethanol (3:1), and the compound-administered group was administered with the compound of Formula 2 dissolved in a solution of dimethylsulfoxide:ethanol (3:1) in an amount of 10 mg/kg. 7-week old male ICR mice in which diabetes was not induced were grouped as a normal group (n=3), and the normal group was administered with 0.2 ml of a solution of dimethylsulfoxide:ethanol (3:1). The normal group, the control group, and the compound-administered group were orally administered three times per one week, and the entire administration period was 2 weeks. Administration-completed mice were sacrificed by cervical dislocation, and then the amount of the sorbitol in the sciatic nerve was measured by HPLC (see FIG. 8).

Figure 8:
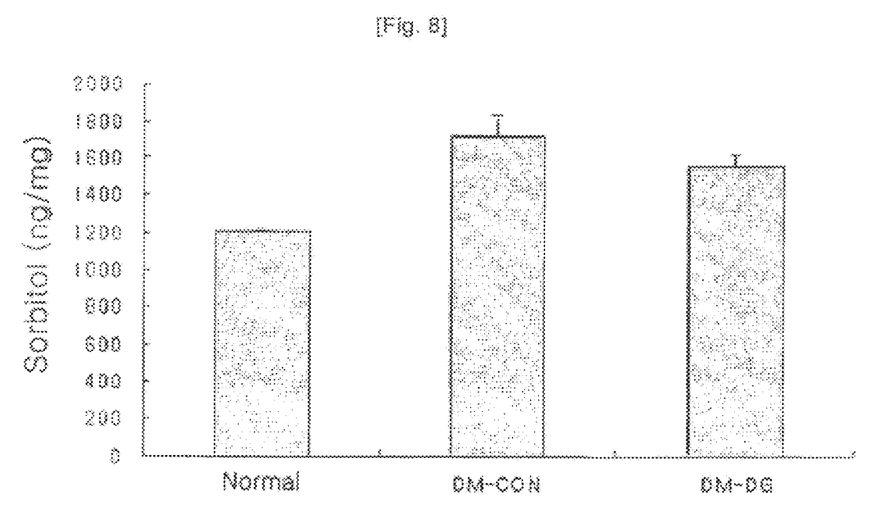
FIG. 8 is a graph illustrating a change in the level of sorbitol in the sciatic nerve of a diabetes-induced mouse resulting from administration of a compound isolated from an extract according to an embodiment of the present invention.

A polyol pathway refers to a process in which glucose is converted to sorbitol by aldose reductase and the sorbitol is changed into fructose by sorbitol dehydrogenase. In a hyperglycemic state, such as diabetes, excess glucose enters cells and sorbitol is generated and accumulated by the polyol pathway. At this time, nerves can be injured by the osmotic operation drawing water into cells. Accordingly, as a result of measuring the effect of the compound according to the present invention on the sorbitol accumulation in the sciatic nerve of the diabetes-induced mouse, as shown in FIG. 8, it was found that the sorbitol in the sciatic nerve of the diabetes-induced control group (DM-CON) was about 40% higher than that of the normal group, but the sorbitol in the sciatic nerve of the compound-administered group (DM-DG) was 10% lower than that of the diabetes-induced control group (DM-CON). Such results show that the compound according to the present invention can partially decrease aggressive factors causing nerve injury.

EXPERIMENTAL EXAMPLE 7

Histological Comparison of Sciatic Nerve of Diabetes-Induced Mouse

The therapeutic effect of the compound according to the present invention on the neuropathy was identified by measuring a histological change of the sciatic nerve.

7-week old male ICR mice underwent alimentary abstinence for 18 hours, and then alloxan dissolved in a physiological saline was once injected to them by intraperitoneal injection in an amount of 160 mg/kg to induce diabetes. Mice that maintained their fasting blood sugar to 200 mg/dl or more for one week, that is, diabetes-induced mice were selected and then divided into a control group (n=5), an extract-administered group (n=5), and a compound-administered group (n=3). The control group was injected with 0.2 ml of a solution of dimethylsulfoxide:ethanol (3:1), the extract-administered group was administered with the extract obtained according to Example 1 dissolved in a solution of dimethylsulfoxide:ethanol (3:1) in an amount of 100 mg/kg, and the compound-administered group was administered with the compound of Formula 2 dissolved in a solution of dimethylsulfoxide:ethanol (3:1) in an amount of 10 mg/kg. All groups were treated three times by oral administration per one week, and the entire administration period was 2 months. Administration-completed mice were sacrificed by cervical dislocation, and then the sciatic nerve was separated, dyed according to the following conditions, and then observed using a 600×, 1200× confocal microscope.

Figure 9:
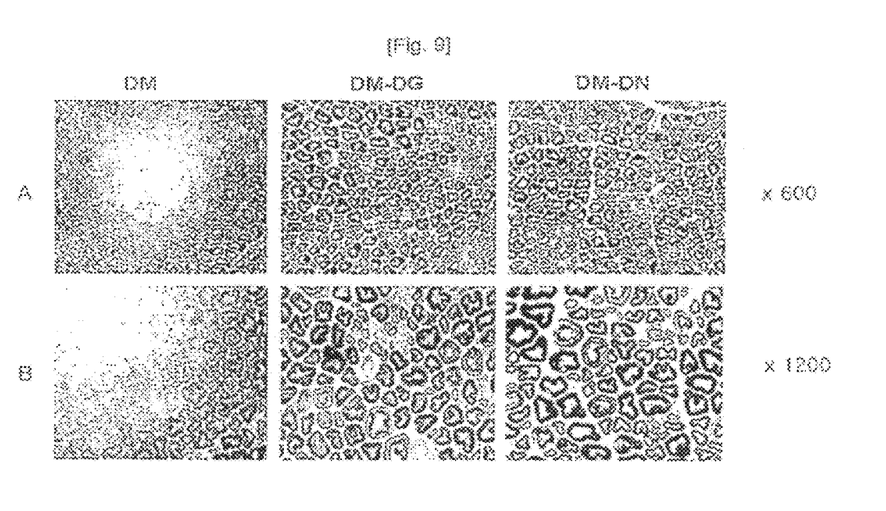
FIG. 9 is images illustrating histological changes in the sciatic nerve of a diabetes-induced mouse resulting from administration of an extract according to an embodiment of the present invention and a compound isolated from the extract.

(1) prefixing: 2.5% glutaraldehyde, 12 or more hours
(2) washing: pH 7.4, 0.1M phosphate buffer solution, 15 minutes/twice
(3) postfixing: 1% OsO4 osmium tetroxide, 60 minutes
(4) washing: pH 7.4, 0.1M phosphoate buffer solution, 5 minutes/twice
(5) dehydrating:
50, 70, 80, 90% alcohol: 10 minutes/each
100% alcohol: 15 minutes/twice
(6) substituting: prophylene oxide, 15 minutes/twice
(7) permeating: propylene oxide (1), EPOK 812 (2), 12 or more hours
(8) embedding: refined EPOK 812 (80° C. polymerization): 12 or more hours
(9) sectioning: semi-thin section, 35-95□
(10) dyeing: 1% toluidine blue FIGS. 9A and 9B show the results obtained with 600 magnification (9A) and 1200 magnification (9B), respectively. In the diabetes-induced group (DM), the axon and the myelin in the central part of the sciatic nerve were significantly destructed. However, in the compound-administered group (DM-DG) and the extract-administered group (DM-DN), the axon and the myelin in the central part of the sciatic nerve were clearly observed. Such results show that the extract or compound according to the present invention can protect and treat nerves injured by the neuropathy.

The compound according to the present invention was formulated into the following forms. However, these formulation examples are for illustrative purposes only and are not intended to limit the scope of the present invention.

FORMULATION EXAMPLE 1

Tablet Formation

| | |
|---|---|
| Compound of Formula 2 | 200 mg |
| Lactose | 100 mg |
| Starch | 100 mg |
| Magnesium stearate | proper |

These components were mixed and compressed into tablets according to a conventional tablet formulating method.

FORMULATION EXAMPLE 2

Liquid Formulation

| | |
|---|---|
| Compound of Formula 2 | 1000 mg |
| CMC-Na | 20 g |
| Isomerized sugar | 20 g |
| Lemon flavor | proper |

Purified water was added so that the volume of the entire solution was 1000 □. These components were mixed according to a conventional liquid formulation method, filled into a brown bottle, and sterilized, thereby producing the liquid formulation.

FORMULATION EXAMPLE 3

Capsule Formulation

| | |
|---|---|
| Compound of Formula 2 | 300 mg |
| Crystalline cellulose | 3 mg |
| Lactose | 14.8 mg |
| Magnesium stearate | 0.2 mg |

These components were mixed according to a conventional capsule formulating method, and then filled to a gelatin capsule, thereby producing the capsule formulation.

FORMULATION EXAMPLE 4

Injection Formulation

| | |
|---|---|
| Compound of Formula 2 | 300 mg |
| Mannitol | 180 mg |
| Injectable sterile distilled water | 2974 mg |
| Na$_2$HPO$_4$12H$_2$O | 26 mg |

An injection containing the components having amounts described above per one ample (2 □) was manufactured according to a conventional injection manufacturing process.

The invention claimed is:

1. A method for treating a multiple neuropathy through deriving neurite outgrowth and increasing secretion of endogenous nerve growth factor, comprising administering to a subject in need thereof a pharmaceutical composition comprising a therapeutically effective amount of an extract of a family Dioscoreaceae and a pharmaceutically acceptable carrier, the family Dioscoreaceae being at least one selected from the group consisting of *Dioscorea nipponica, Dioscorea septembloba, Dioscorea quinqueoloba, Dioscorea batatas, Dioscorea japonica, Dioscorea bulbifera, Dioscorea tokoro,* and *Dioscorea tenuipes,* wherein the extract is obtained by performing an extraction process which comprises extracting a root of the family Dioscoreaceae with a first extraction solvent selected from the group consisting of water, $C_1$-$C_4$ alcohol, and a mixture of water and a $C_1$-$C_4$ alcohol.

2. The method of claim 1, wherein the family Dioscoreaceae is *Dioscorea nipponica, Dioscorea quinqueoloba,* or *Dioscorea tokoro.*

3. The method of claim 1, wherein the first extraction solvent is a mixture of water and methanol or a mixture of water and ethanol.

4. The method of claim 1, wherein the extraction process further comprises dispersing the extract obtained by the extraction with the first extraction solvent in water, and extracting with a second extraction solvent of water-saturated $C_1$-$C_4$ alcohol.

5. The method of claim 4, wherein the second extraction solvent is water-saturated butanol.

6. A method for treating a multiple neuropathy through deriving neurite outgrowth and increasing secretion of endogenous nerve growth factor, comprising administering to a subject in need thereof a pharmaceutical composition comprising a therapeutically effective amount of a compound represented by Formula 1 or salt thereof; and a pharmaceutically acceptable carrier:

[Formula 1]

wherein R is a hydrogen atom, a $C_1$-$C_4$ alkyl group, or a saccharide.

7. The method of claim 6, wherein R is a hydrogen atom.

* * * * *